United States Patent [19]

Munny

[11] 4,379,350
[45] Apr. 12, 1983

[54] PROSTHETIC JOINT FOR KNEE AND ABOVE-KNEE AMPUTEES

[76] Inventor: Günter Munny, Wipperfürther Str. 49, 5064 Odenthal-Eikamp, Fed. Rep. of Germany

[21] Appl. No.: 268,719

[22] Filed: Jun. 1, 1981

[30]    Foreign Application Priority Data

Feb. 11, 1981 [EP]   European Pat. Off. ........ 81100947.1

[51] Int. Cl.³ .......................... A61F 1/04; A61F 1/08
[52] U.S. Cl. ............................................. 3/22; 3/17 R
[58] Field of Search ...................................... 3/22–29, 3/2, 17 R

[56]        References Cited

U.S. PATENT DOCUMENTS

| | | | |
|---|---|---|---|
| 1,586,015 | 5/1926 | Underwood | 3/17 R |
| 2,046,069 | 6/1936 | Greissinger | 3/29 |
| 2,457,482 | 12/1948 | Marean | 3/29 |
| 3,597,767 | 10/1971 | Prahl | 3/22 |
| 3,928,873 | 12/1975 | Zevering | 3/27 |
| 4,085,466 | 4/1978 | Goodfellow et al. | 3/22 X |
| 4,312,081 | 1/1982 | Munny | 3/22 |

FOREIGN PATENT DOCUMENTS

| | | | |
|---|---|---|---|
| 828292 | 1/1952 | Fed. Rep. of Germany | 3/22 |
| 851394 | 10/1952 | Fed. Rep. of Germany | 3/22 |
| 978586 | 12/1964 | United Kingdom | 3/21 |

*Primary Examiner*—Ronald L. Frinks
*Attorney, Agent, or Firm*—Reising, Ethington, Barnard, Perry, Brooks & Milton

[57]         ABSTRACT

A prosthetic joint for knee and above-knee amputees consists of a hollow shank (1), open at the top, for receiving the femoral stump, of an attachment member (3) articulatedly joined to this shank for fitting of a below-knee prosthesis (2) with a foot part and of an articulated joint between the shank (1) and the attachment member (3).

The articulated joint consists of a guide member (5) connected to the attachment member (3) and having rectilinear guide grooves (17a, 17b), of a support (7) guided shiftably in said guide member by means of arcuate guide bars (18a, 18b) and connected rigidly to the shank (1), and of a gearing located between the support and the guide member.

The gearing consists of an arcuate rack (8) on the support (7), of a rectilinear rack (10) on the guide member (5) and of a pinion (9) rotatably mounted in the slide member (6) and engaging the two racks.

8 Claims, 4 Drawing Figures

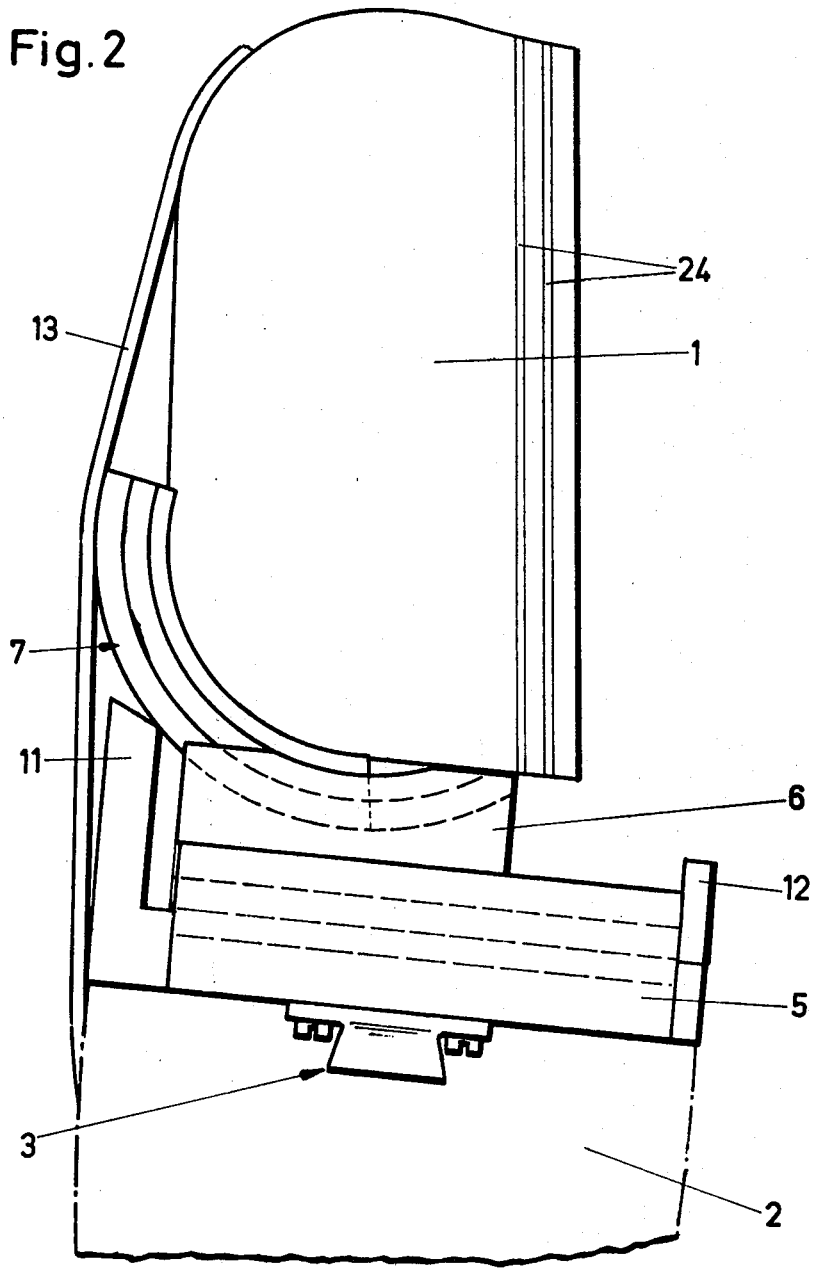

PROSTHETIC JOINT FOR KNEE AND ABOVE-KNEE AMPUTEES

The invention relates to a prosthetic joint for knee and above-knee amputees, which consists of a hollow shank, open at the top, for receiving the femoral stump and of an attachment member articulated by joints to this shank, for fitting of a below-knee prosthesis with a foot part.

The shank is made by means of a cast taken of the intact femoral stump and is then pushed over this stump during use and connected firmly thereto, in a way known per se, by means of holding straps or the like. A tube adaptor covered with a so-called cosmetic made of foam material is fastened to the attachment member in an appropriate way.

The prosthetic joints used hitherto for these purposes are, on the one hand, too heavy and are therefore cumbersome to wear. On the other hand, the known prosthetic joints have the disadvantage that, when the below-knee prosthesis is bent at an angle, it can be seen clearly that it is a prosthesis. When these known prosthetic joints are bent at an angle, differences in length between a healthy leg and the prosthesis become visible; and sharp edges or projections protrude in the front at the point where the knee-cap is located on the natural leg.

Accordingly, the object on which the invention is based is to provide an improved prosthetic joint for knee and above-knee amputees, which does not possess these disadvantages, that is to say, which has a low weight and is nevertheless stable and which is more dynamic in the walking phase and permits better so-called cosmetics.

This object is achieved, according to the invention, due to the fact that the articulated joint comprises a guide member rigidly connected to the attachment member and having rectilinear guide grooves, a slide member guided slidably in said guide member, a support guided shiftably in said slide member by means of arcuate guide bars, which support is connected rigidly to the shank, and a gearing located between the arcuate support, on the one hand, and the guide member, on the other hand. This gearing consists of an arcuate rack on the support, a rectilinear rack on the guide member and a pinion rotatably mounted in the slide member and engaging the two racks. The gearing effects a forward displacement of the slide member and, thereby, of the shank upon a pivotal movement of the shank relative to the attachment member.

Consequently, this prosthetic joint is a so-called rotary sliding joint. Therefore, not only is a simple rotary movement about a fixed axis brought about, but, at the same time, a forward displacement of the slide member, and, thereby, of the shank is induced by means of the special arrangement of the gearing.

For the case where the forward displacement of the slide member, caused by a pivoting of the shank through 90° relative to the below-knee prosthesis, is too small or too large, it is proposed that the pinion should have two gear wheels which are arranged next to one another and coaxially and have different reference-circle diameters, one of which engages the arcuate rack on the support and the other the rectilinear rack on the guide member. In this way, a stepping-down or stepping-up can be achieved in a simple way, and the anatomically correct forward displacement of the slide member and, thereby, the shank, can be produced.

In this case, one of the two gear wheels preferably consists of two halves which are located on both sides of the other gear wheel. Two racks are then assigned to the two gear-wheel halves. As a result of this arrangement, a uniform and symmetrical distribution of forces is achieved.

To prevent the attachment member supporting the below-knee prosthesis, in the prosthetic joint, from being detached from the shank and, thereby, from the femoral stump, all known retaining means can be used. However, it is preferably envisaged that the support fastened to the shank should be surrounded on both sides, at its underside, by the slide member in a C-shaped manner.

It is proposed, correspondingly, that there be provided, in the guide member connected to the below-knee prosthesis, grooves into which engage corresponding outwardly projecting guide bars of the slide member, so that these guide bars are surrounded likewise in a C-shaped manner. Consequently, it is impossible to detach unintentionally a joint designed in this way.

It is also envisaged, preferably, that the slide member and/or the guide member and/or the support should consist of materials having low mutual friction values, preferably plastics. In this case, special lubrication, which would otherwise present problems with regard to soiling of the trouser leg, can then be dispensed with.

To limit the pivotal movement of the prosthetic joint, stops are fastened at the front and at the rear end of the guide member.

Also provided is an elastic strip which covers the prosthetic joint on the front side and is fastened at the top of the shank and at the bottom of the attachment member and which covers these two parts over a relatively long length, but which, above all, covers the components of the prosthetic joint.

The below-knee prosthesis can be connected to the attachment member in a way known per se. Preferably provided there, for adjustable fitting, is a retaining pin which widens conically downwards and which, by means of countermembers, known per se, enables the below-knee prosthesis to be aligned and adjusted to a certain extent.

A further adjustment in a lateral direction is possible, due to the fact that a series of several rows of threaded bores, located at regular intervals, is provided in the guide member. The attachment member can then be screwed on, offset more or less to the side, depending on the static conditions.

If the guide member is made of plastic, a secure retention, without loosening of the screw connection, is ensured by means of a metallic reinforcing plate which is let into the guide member and which contains the threaded bores.

Finally, to achieve also a secure connection between the shank and the femoral stump, several grooves are provided at the upper margin of the shank on its outside.

The invention is explained in more detail below in two exemplary embodiments with reference to the drawings in which:

FIG. 2 shows a side view of the prosthetic joint according to FIG. 1, but in a state bent at an angle;

Figure 1:
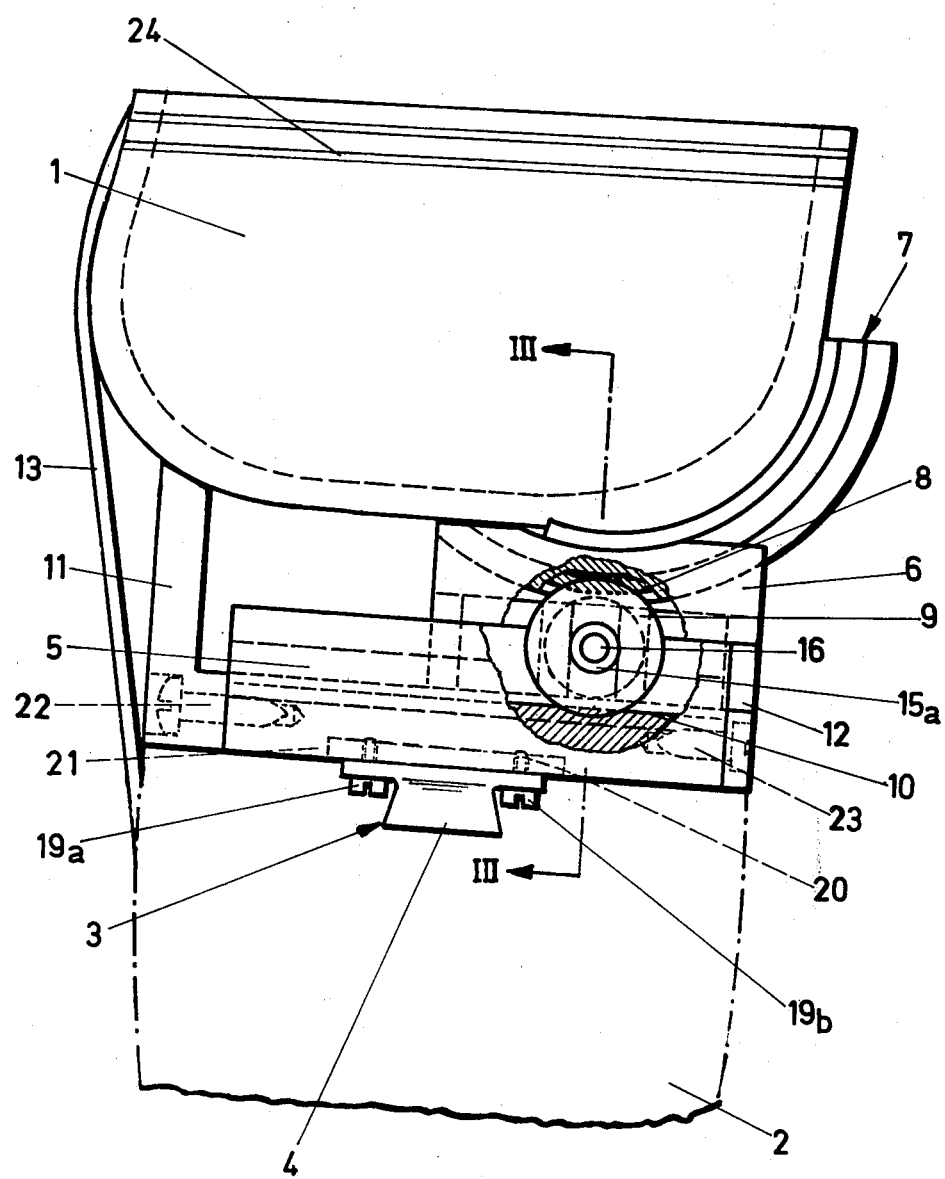
FIG. 1 shows a side view of a prosthetic joint according to the invention, in the extended state.

As may be seen from the drawing, the prosthetic joint consists of a hollow shank 1, open at the top, which is pushed onto the femoral stump and which is connected rigidly to the latter in a way known per se. The connection is further improved by means of the retaining grooves made in the shank. The shank consists of plastic and was made beforehand from a cast taken of the femoral stump.

The joint also comprises an attachment member 3 which consists of a retaining plate and of a retaining pin 4 connected integrally to the latter at the underside and permitting adjustable fitting of the below-knee prosthesis 2.

Furthermore, the prosthetic joint comprises an articulated joint between shank 1 and the attachment member 3. This articulated joint consists of a guide member 5 connected rigidly to the attachment piece and having rectilinear guide grooves 17a and 17b. As may be seen from FIG. 1, the attachment member 3 is screwed to the guide member by means of fastening screws 19a and 19b. In this case, the screws are screwed into those threaded bores in a metal reinforcing plate 21 let into the guide member, which give the attachment member 3 the correct position.

Figure 3:
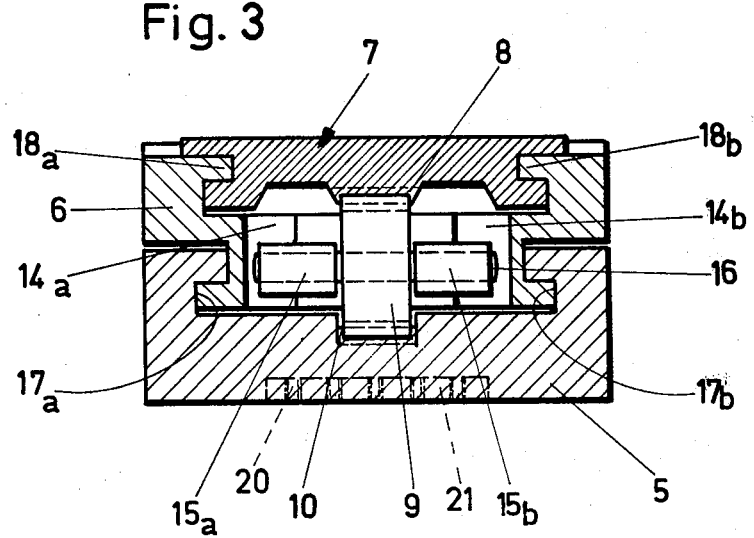
FIG. 3 shows a section along the line III—III in FIG. 1.

As may be seen from FIG. 1 together with FIG. 3, the articulated joint is formed by an arcuate support 7 with laterally projecting circular guide bars 18a and 18b. This support is fastened, at the rear, to the lower end of the shank 1. As may be seen from FIG. 3, said guide bars are surrounded in a C-shaped manner by the slide member 6 provided appropriately with a groove.

If the guide member 5 were connected rigidly to the slide member 6, only a simple pivotal movement of the prosthetic joint would be possible. To achieve a desired forward movement in addition, the slide member is provided, at the bottom, with outwardly projecting guide bars which engage into corresponding guide grooves 17a and 17b in the guide member 5. These guide bars and guide grooves are made rectilinear and permit a rectilinear displacement of the slide member 6 relative to the guide piece 5, as may be seen by comparing FIGS. 1 and 2.

A gearing located between the aforesaid parts serves to ensure coordination of the forward movement and of the pivotal movement. In the exemplary embodiment according to FIGS. 1 to 3, this gearing consists of an arcuate rack 8 in the support, specifically in the middle between the two circular guide bars 18a and 18b projecting laterally from said support.

The gearing also consists of a pinion 9 located rotatably on a fixed axle 16 which is clamped, via clamping sleeves 15a and 15b made of plastic, into appropriate retaining slots 14a and 14b in the slide member 6. The pinion engages at the top, the arcuate rack 8 of support 7, but, on the other side, also a rectilinear rack 10 located in the guide member 5 between its two guide grooves 17a and 17b.

The result of this arrangement is that, when the shank 1 is pivoted out of the position shown in FIG. 1 into the position shown in FIG. 2, the arcuate rack 8 turns the pinion 9, so that the latter necessarily has to roll on the rectilinear rack 10 of the guide member 5. The result of this is that the pinion 9 drives its shaft 16 and, thereby, the slide member 6, connected to this shaft, in the same direction. However, since the slide member 6 has in its upper part, on both sides, arcuate guide grooves in which the arcuate guide bars 18a and 18b of the support 7 are located, this support 7 is also necessarily included in the forward movement and thereby moves the shank 1 forwards, or, if the position of the shaft 1 connected to the femoral stump is assumed to be fixed, forces a backward movement of the below-knee prosthesis 2. In any case, the result of this rotary and sliding movement induced by the prosthetic joint according to the invention is that the below-knee prosthesis moves relative to the femoral stump practically in the same way, during a pivoting action, as in the case of an undamaged knee.

Fastened to the front and rear end of the guide member are stops 11 and 12 which limit, to both sides, the movement of the slide member 6 and, thereby, also the pivotal movement between the shank 1 and the below-knee prosthesis 2. These stops are fastened to the guide member by means of fastening screws 22 and 23 respectively.

To obtain a completely smooth finish at the front, the joint is covered by an elastic strip 13 which is connected fixedly to the shank and to the attachment member respectively at its two ends and which covers the gap between these two parts.

Figure 4:
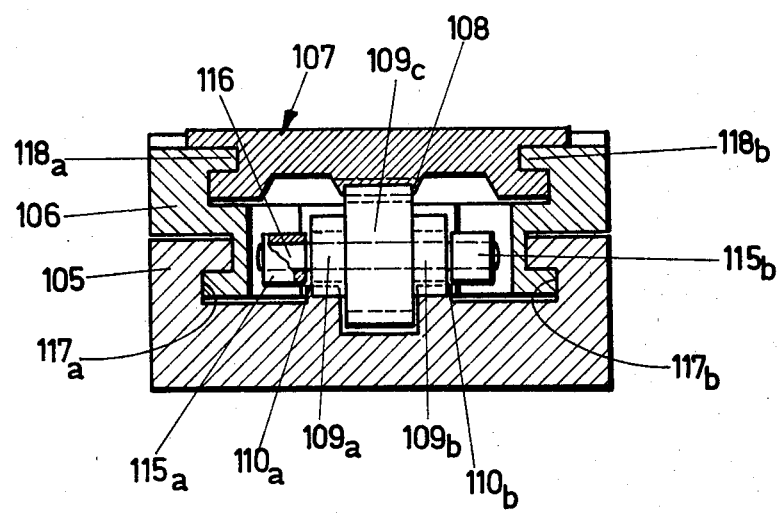
FIG. 4 shows a section analogous to FIG. 3 through a modified embodiment.

In the modified embodiment illustrated in FIG. 4, a gearing with a different stepping-up is provided. This gearing comprises an arcuate rack 108 in the support 107 and a gear wheel 109c which engages this rack and which rests loosely on a fixed axle 116, the latter being, again, located in appropriate retaining slots of the slide member 106 by means of clamping sleeves 115a and 115b and being connected fixedly to this slide member. Located on both sides of this gear wheel 109c are two further gear wheels 109a and 109b which are likewise arranged freely rotatably on the shaft 116, but are connected to the middle gear wheel 109c in a manner fixed against rotation. The three gear wheels can, of course, also be made from one piece.

Whereas the middle gear wheel 109c engages exclusively the upper arcuate rack 108, but runs freely at the bottom, the two smaller gear wheels 109a and 109b rotating at its side engage, at the bottom, two rectilinear racks 110a and 110b in the guide member 105. Consequently, a stepping-up of movements now takes place, and this results from the different reference-circle diameters of the middle gear wheel 109c on the one hand, and of the two lateral gear wheels 109a and 109b, on the other hand.

Here, too, circular guide bars 118a and 118b on the slide member 106 again engage into appropriately shaped guide grooves in the support 107, whilst, on the other hand, rectilinear guide grooves 117a and 117b in the guide member 105 receive the corresponding guide bars, projecting at the bottom, outwards from the slide member 106.

It is also noted that the prosthetic joint according to the invention for knee and above-knee amputees can be used with different above-knee sizes, because the shank can be made in different sizes.

I claim:

1. Prosthetic joint for knee and above-knee amputees, comprising a hollow shank (1), open at the top for receiving the femoral stump and, articulatedly joined to this shank, an attachment member (3) for fitting of a below-knee prosthesis (2), wherein the articulated joint comprises a guide member (5, 105), connected rigidly to the attachment member (3) and having rectilinear guide grooves (17a, 17b; 117a, 117b), a slide member (6, 106) guided slidably in said guide member, a support (7, 107)

guided shiftably in said slide member by means of arcuate guide bars (18a,18b;118a,118b), which support is connected rigidly to the shank (1), and a gearing located between the arcuate support (7, 107), on the one hand, and the guide member (5,105) on the other hand, the gearing consisting of an arcuate rack (8,108) on the support (7, 107), a rectilinear rack (10;110a,110b) on the guide member (5, 105) and a pinion (9, 109) rotatably mounted in the slide member (6, 106) and engaging the two racks (8,108;10,110a,110b), the gearing effecting a forward displacement of the slide member (6, 106) and, thereby, of the shank (1) upon a pivotal movement of the shank (1) relative to the attachment member (3).

2. Prosthetic joint according to claim 1, wherein the pinion (109) has two gear wheels which are located next to one another and coaxially and have different reference-circle diameters and one (109c) of which engages the arcuate rack (108) on the support (107) and the other (109a) the rectilinear rack (110a) on the guide member (105).

3. Prosthetic joint according to claim 2, wherein one of the two gear wheels consists of two halves (109a, 109b) which are located on both sides of the other gear wheel (109c), and in that two racks (110a, 110b) are assigned to these halves.

4. Prosthetic joint according to any one of claims 1, 2 or 3, wherein the support (7, 107) fastened to the shank (1) is surrounded on both sides, at the underside, by the slide member (6, 106) in a C-shaped manner.

5. Prosthetic joint according to any one of claims 1, 2 or 3, having stops (11, 12) fastened to the front and rear end of the guide member (5, 105), for limiting the pivotal movement of the prosthetic joint.

6. Prosthetic joint according to claim 1, having a series of several pairs of threaded bores (20) in the guide member (5, 105), which are arranged at regular intervals.

7. Prosthetic joint according to claim 6, having a metallic reinforcing plate (21) let into the guide member (5) on the underside, for receiving the threaded bores (20).

8. Prosthetic joint according to claim 1, having grooves (24) at the upper margin of the shank (1) on its outside.

* * * * *